United States Patent
Booher

(10) Patent No.: US 7,749,531 B2
(45) Date of Patent: Jul. 6, 2010

(54) APPARATUS AND METHOD FOR DETECTING BACTERIAL GROWTH BENEATH A WOUND DRESSING

(75) Inventor: Jon Booher, Lake Forest, CA (US)

(73) Assignee: Indicator Systems International, San Clemente, CA (US)

( * ) Notice: Subject to any disclaimer, the term of this patent is extended or adjusted under 35 U.S.C. 154(b) by 919 days.

(21) Appl. No.: 11/148,131

(22) Filed: Jun. 8, 2005

(65) Prior Publication Data

US 2007/0003606 A1 Jan. 4, 2007

(51) Int. Cl.
*A61F 13/00* (2006.01)
*A61M 25/02* (2006.01)
*G01N 33/48* (2006.01)

(52) U.S. Cl. .................. 424/443; 600/433; 422/58

(58) Field of Classification Search .............. 424/443; 600/433; 422/58
See application file for complete search history.

(56) References Cited

U.S. PATENT DOCUMENTS

| | | | |
|---|---|---|---|
| 3,899,295 A | | 8/1975 | Halpern |
| 4,222,745 A | | 9/1980 | Cloyd |
| 4,269,804 A | | 5/1981 | Kring |
| 4,285,697 A | | 8/1981 | Neary |
| 5,407,829 A | | 4/1995 | Wolfbeis et al. |
| 5,437,622 A | * | 8/1995 | Carion ................ 602/57 |
| 5,498,528 A | | 3/1996 | King |
| 5,753,285 A | | 5/1998 | Horan |
| 6,149,952 A | * | 11/2000 | Horan ................ 426/87 |
| 6,495,368 B1 | | 12/2002 | Wallach |
| 6,562,297 B1 | | 5/2003 | Bonstein et al. |
| 6,589,761 B1 | | 7/2003 | Freadman et al. |
| 6,924,147 B2 | | 8/2005 | Kelly et al. |
| 7,014,816 B2 | | 3/2006 | Miller et al. |
| 7,183,455 B2 | | 2/2007 | Utsugi |
| 2003/0060479 A1 | * | 3/2003 | Brown et al. ............ 514/282 |
| 2003/0064422 A1 | | 4/2003 | McDevitt et al. |
| 2003/0199783 A1 | | 10/2003 | Bloom et al. |
| 2003/0203011 A1 | * | 10/2003 | Abuelyaman et al. ....... 424/445 |
| 2004/0044299 A1 | * | 3/2004 | Utsugi ................ 602/58 |
| 2004/0115319 A1 | | 6/2004 | Morris et al. |

FOREIGN PATENT DOCUMENTS

IE 20040542 2/2006

OTHER PUBLICATIONS

Soken Chemical and Engineering Co., Ltd., http://www.soken-ce.co.jp/english/nencyaku/lineup-index.html, archived web pages from 2004 for SK Dyne pressure-sensitive adhesives, printed from the Internet on Mar. 11, 2009.*

* cited by examiner

*Primary Examiner*—Karen Cochrane Carlson
*Assistant Examiner*—Rosanne Kosson
(74) *Attorney, Agent, or Firm*—Swiss Tanner, P.C.

(57) ABSTRACT

An apparatus and method are provided for visually monitoring, detecting, and/or determining the presence, absence, and/or growth of harmful or potentially harmful bacterial microorganisms beneath a wound dressing, in one example used to cover an indwelling central venous catheter or other catheter. A bacteria detection apparatus includes a barrier membrane, a permeable membrane for placement proximate a wound or a catheter insertion site, and an indicator between the barrier membrane and the permeable membrane for indicating the presence of bacteria proximate the permeable membrane. A method of using a bacterial growth detection apparatus is also provided.

24 Claims, 2 Drawing Sheets

APPARATUS AND METHOD FOR DETECTING BACTERIAL GROWTH BENEATH A WOUND DRESSING

TECHNICAL FIELD

The present invention relates generally to medical indicator devices and, more particularly, to an apparatus and method for detecting bacterial microorganisms related to a wound dressing or a dressing used to cover an indwelling catheter.

BACKGROUND

Central venous catheters and other catheters inserted through the skin and into the lumen of an artery or vein are widely used in a variety of patients usually in the hospital setting. They provide secure and immediate venous access and allow for the safe administration of fluids and drugs. However, catheter related bloodstream infection (CR-BSI) is a serious and potentially life-threatening complication when catheters and insertion sites become infected with bacterial microorganisms. The insertion sites for these catheters are routinely covered with a dressing as a preventive measure for bacterial infections.

Intravascular catheters are employed routinely in healthcare settings for a number of purposes including infusion of pharmacological drugs and fluids, hemodialysis, monitoring of pressures, and sampling of blood. Although these catheter devices are essential components of modern day medical care, they are also susceptible to microbial contamination. Microbial pathogens can attach to the catheter surface at the site of penetration into the skin. A number of factors renders catheter implants especially susceptible to microbial contamination. Firstly, the catheter essentially compromises the skin's natural protective barrier, providing a direct route to bypass the body's first line of immunity. In addition, upon insertion into the host, the outer surface of the catheter is quickly covered with host proteins that facilitate microbial attachment. There is also evidence that implanted abiotic material itself causes local attenuation of antimicrobial immune responses, thereby providing a fertile breeding ground for microbial biofilm formation. Finally, patients who possess the greatest need for catheterization are often immunologically compromised and are therefore more susceptible to bacterial infection.

Catheters themselves are generally infected via one of two general routes, typically by organisms that compromise the natural flora surrounding the site of catheter insertion. First, microbes may contaminate the catheter along its outer surface, and it is believed that this type of infection often occurs during the initial insertion of the catheter through the skin. Catheters can also be contaminated in their lumenal compartments where fluids flow from contaminated infusate solutions. The most prevalent bacteria found to be the cause of bacterial sepsis from the exterior flora surrounding the insertion site include, but are not limited to, coagulase negative Staphylocci, *Staphylococcus epidermitus, Staphylococcus aureus, Escherichia coli, Enterobacter cloacae* and *Pseudomonas aeruginosa*.

Catheter-related bloodstream infections are notoriously difficult to treat via conventional antibiotic therapy, with associated mortality rates ranging from 12% to 25%. Catheter related bloodstream infection is the most frequent serious complication seen with catheters with infections occurring in as many as 3% to 7% of all catheter placements, which is estimated to be more than 250,000 patients in U.S. hospitals each year. In addition, these infection complications extend hospital stays, necessitate active intervention on the part of healthcare personnel, and result in driving the estimated annual domestic healthcare cost associated with complications arising from these catheter-related infections to more than nine billion dollars.

The presence and growth of harmful and/or potentially harmful bacteria beneath wound dressings or dressings used to cover indwelling central venous catheters has been shown to cause serious infection, illness, and even death if the bacterial growth goes unnoticed and untreated for even a relatively short period of time. The most prevalent pathogenic bacteria found to be the source of septic infections include, but are not limited to, coagulase negative staphylocci, *Staphylococcus epidermitus, Staphylococcus aureus, Escherichia coli, Enterobacter cloacae*, and *Pseudomonas aeruginosa*. These bacteria can enter the blood stream causing serious and life-threatening illness.

Recent advances in catheter compositions have shown to be relatively successful in preventing some bacterial growth. Some catheters have been coated with antibacterial growth materials, chemicals, and drugs in an effort to prevent infections from entering the bloodstream by way of this conduit. Wound dressings used to cover these catheter insertion sites have similarly been treated with antibacterial agents to inhibit bacterial growth. In most cases the effort has been focused on materials and pharmaceuticals used to prevent bacterial growth. Dressings used to cover indwelling catheters in the hospital setting are also routinely changed and the puncture site carefully examined for bacterial infection. However, an apparatus and method for early warning or indication of the presence of harmful bacterial growth has not been available for use with catheters.

Thus, an apparatus and method for detecting and easily indicating bacterial growth-is not presently known but highly desirable.

SUMMARY

The present invention provides an apparatus and method for visually detecting bacterial growth related to wound dressings or catheter insertion sites at an early stage of growth for advantageously remedying the bacterial growth.

In accordance with an embodiment of the present invention, a bacterial growth detection apparatus is provided, the apparatus including a barrier membrane, a permeable membrane for placement proximate a wound, and an indicator between the barrier membrane and the permeable membrane for indicating the presence of bacterial growth proximate the permeable membrane.

In accordance with another embodiment of the present invention, another bacterial growth detection apparatus is provided, the apparatus including a barrier membrane including a transparent hydrophobic polymeric membrane, and a permeable membrane including a transparent hydrophilic polymeric membrane, the permeable membrane for placement proximate a wound or catheter insertion site. The detection apparatus further includes an indicator between the barrier membrane and the permeable membrane, the indicator capable of detecting a pH change caused by byproducts of bacterial growth diffused through the permeable membrane.

In accordance with yet another embodiment of the present invention, a method of detecting bacterial growth is disclosed, the method including providing a bacterial growth detection apparatus as described above, placing the permeable membrane over a wound or catheter insertion site, detecting a pH change caused by byproducts of bacterial growth, and indicating the presence of the byproducts of bacterial growth with a visible change of the indicator.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

Figure 1:
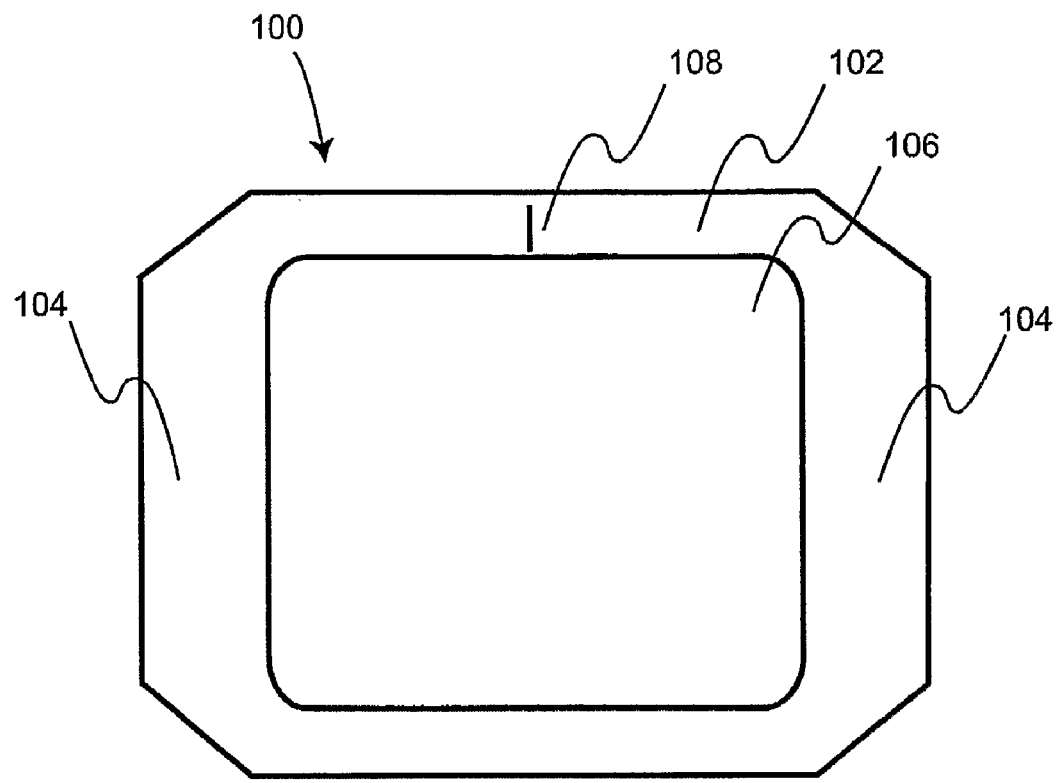
FIG. 1 shows a top view of a bacterial growth detection apparatus in accordance with an embodiment of the present invention.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The present invention provides an apparatus and method for visually monitoring, detecting, and/or determining the presence, absence, and/or growth of harmful or potentially harmful bacterial microorganisms beneath a wound dressing or a catheter insertion site, in one example used to cover an indwelling central venous catheter or other catheter used for insertion into the lumen of an artery or vein or other skin puncture site in which a wound dressing or a catheter insertion site covering may be prescribed and applied.

Various bacterial microorganisms may be detected with the present invention, including but not limited to *Staphylococcus aureus, Staphylococcus epidermitus, Streptococcus mitis, Streptococcus sanguis, Enterococcus faecium, Escherichia coli, Enterobacter cloacae, Enterobacter aerogenes, Enterococcus faecalis, Pseudomonas aeruginosa, Klebsiella pneumonia, Candida albicans*, and gram negative bacilli.

In one embodiment of the present invention, a semipermeable/permeable hydrophilic/hydrophobic polymeric composition of membranes with an indicator layer is incorporated with a wound dressing material for the detection of harmful or potentially harmful bacterial microorganisms. The wound dressing or catheter insertion site material may also be provided with certain coverings which allow for the easy application of the wound dressing to the skin at the site of catheter insertion. Various catheters may be used, including but not limited to those used for central venous access placed in the arm or leg or those used for monitoring, such as the Swan-Ganz catheter used for measuring cardiac output and often placed in the jugular vein. Sterilization of the detection apparatus elements, including a barrier membrane, a permeable membrane, and an adhesive, may be provided using conventional means such as radiation sterilization or gas sterilization procedures. Conventional peel-pack may also be used for each detection apparatus.

Advantageously, the present invention provides an early warning of the presence/growth of harmful or potentially harmful bacterial microorganisms beneath a wound dressing or dressing used to cover an indwelling catheter (e.g., in a hospital setting) such that early detection may prompt intervention to mitigate the microbial growth at an early stage of potential infection.

Figure 2:
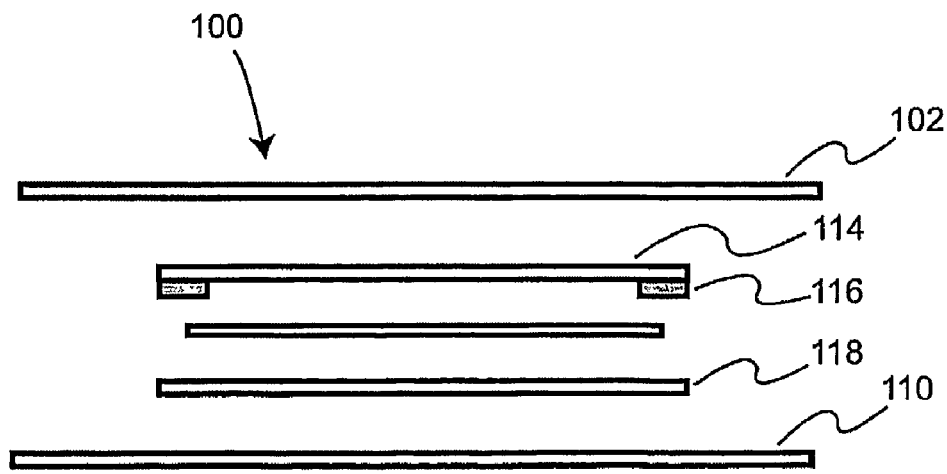
FIG. 2 shows an exploded side view of the bacterial growth detection apparatus of FIG. 1 in accordance with an embodiment of the present invention.
Figure 3:
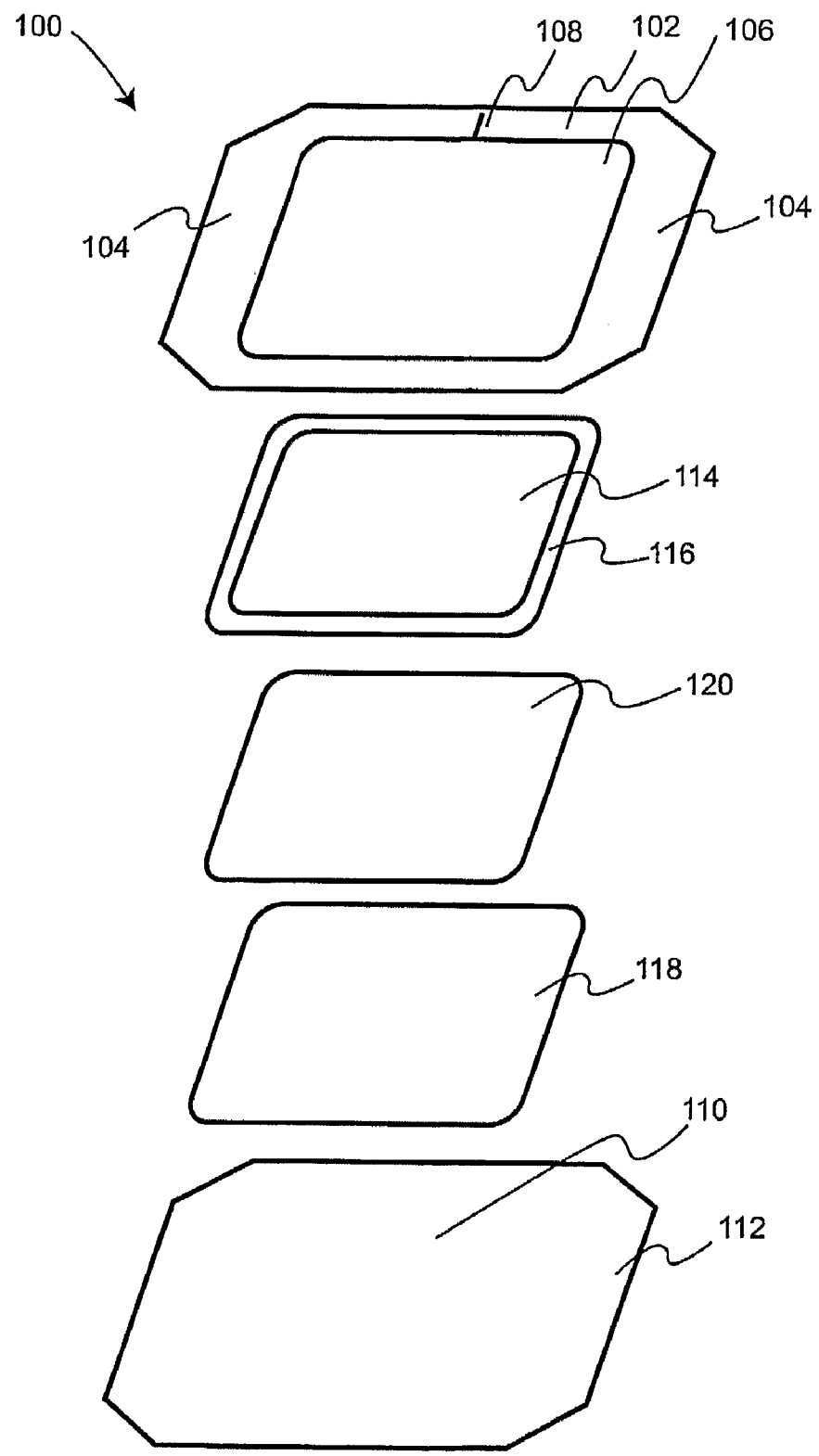
FIG. 3 shows an assembly view of the bacterial growth detection apparatus of FIG. 1 in accordance with an embodiment of the present invention.

Referring now to FIGS. 1, 2, and 3, a top view, an exploded side view, and an assembly view, respectively, of a bacterial growth detection apparatus 100 are shown in accordance with embodiments of the present invention. Detection apparatus 100 includes an indicator 120 between a barrier membrane 114 and a permeable membrane 118. An adhesive 116 is provided around the circumference of barrier membrane 114. Optionally, the present invention may be packaged between sheet liners 102 and 110.

In one example, barrier membrane 114 is a transparent, hydrophobic, and polymeric barrier membrane that acts as a barrier to the outside environment. Water, water vapor, and/or bacterial growth are prevented from penetrating to the wound or catheter insertion site from the environment by barrier membrane 114. Barrier membrane 114 does permit the passive diffusion of water vapor and oxygen from under the wound dressing or catheter insertion site to the environment. Barrier membrane 114 further permits the passive diffusion of oxygen from the environment through the barrier membrane to the skin and creates a moist environment at the surface of the skin and wound or catheter insertion site while limiting water vapor loss from the underlying tissue.

The term "barrier composition" or "barrier membrane" is used throughout the specification to describe a transparent hydrophobic polymeric membrane which is used as the outermost component of the wound dressing or catheter insertion site when applied to the skin and is used to prevent water or water vapor or bacteria from penetrating through the outer layer from the environment and to the wound or catheter insertion site. This polymeric barrier permits the passive diffusion of water vapor and oxygen from under the wound dressing to the environment. It further permits the passive diffusion of oxygen from the environment through the barrier membrane to the skin and creates a moist environment at the surface of the skin and wound or catheter insertion site while limiting water vapor loss from the underlying tissue.

Barrier compositions or membranes/films which may be used in accordance with the present invention include but are not limited to poly(vinylidene fluoride), poly(vinylidene chloride), phenoxy resins, butadiene/styrene copolymers, butadiene/methylstyrene copolymers, poly(meth)acrylates, butadiene/acrylonitrile copolymers, ethylene/propylene copolymers, polybutadiene, polyisoprene, poly(oxy-2,6-dimethyl-1,4-phenylene), poly(oxycarbonyloxy-1,4[1,4-phenyleneisopropylidene-1,4-phenylene), acrylonitrile styrene copolymers, acrylonitrile/methyl acrylate/butadiene copolymers, acrylonitrile/styrene/butadiene copolymers, poly-1-vinylaphthalene, polyvinylphenyl ketone, poly-p-xylenedodecanedioate, poly-tetramethylene octenediamide, poly-tetramethylene terephthalene, poly-trimethylene-3,3'-dibenzoate, poly-terephthallic anhydride, poly-4-methyl-diamine, polyvinylene carbonate, polyvinylene laurate, polyisopropenyl acetate, polyallylbenzene, polyvinylbutyl ether, polyvinyl formate, polyvinyl phenyl ether, polynorbornadine, polycarbonate, hydrophobic polyesters and polyurethanes, and mixtures thereof.

Barrier membrane 114 includes an adhesive 116 that is used to contact the skin and make a secure bond that is a perimeter of adhesion substantially along the border of barrier membrane 114. Adhesive 116 is a medical grade adhesive along the circumference/border of barrier membrane 114 and prevents apparatus 100 from being dislodged or inadvertently removed from the skin.

Permeable membrane 118 is beneath (i.e., closer to the wound or catheter insertion site or skin) barrier membrane 114 and, in one example, is a second transparent, permeable or semipermeable, hydrophilic, and polymeric membrane. Permeable membrane 118 does not extend fully to the margins of barrier membrane 114 but is held in place by adhesive 116 used to secure the wound dressing and indicator to the skin. Permeable membrane 118 is permeable to gases, water vapor, and gases dissolved in water vapor in one example. In yet another example, permeable membrane 118 is permeable to gases that include, oxygen, carbon dioxide, carbon monoxide, hydrogen sulfide, hydrogen, sulfur dioxide and ammonia among others, such that the concentration of gas which may ultimately diffuse through the polymeric composition is sufficient to produce a visual colorimetric reaction with indicator 120 which is contained or "sandwiched" between the inner permeable membrane 118 and the outer barrier membrane 114.

The term "hydrophilic semipermeable polymeric composition" or "permeable membrane" is used to describe the chemical composition of the transparent membrane that is in closer proximity to the skin and the wound or catheter insertion site than the barrier membrane. The permeable membrane may be in contact with the skin at most of its surface that is proximal to the skin. This membrane is permeable to gases, water vapor and gases dissolved in water vapor. It is permeable to gases including but not limited to oxygen, carbon dioxide, carbon monoxide, hydrogen sulfide, hydrogen, sulfur dioxide, and ammonia among others, such that the concentration of gas which may ultimately diffuse through the polymeric composition is sufficient to produce a visual colorimetric reaction with the indicator which is between the inner semi-permeable membrane and the outer barrier membrane.

A number of hydrophilic, permeable polymers may be used in the present invention, including but not limited to (poly)hydroxyethyl methacrylate, (poly)hydroxypropyl methacrylate, (poly)glycerol methacrylate, copolymers of hydroxyethyl methacrylate, hydroxypropyl methacrylate or glycerol methacrylate and methacrylic acid, aminoacrylate and aminomethacrylate, (poly)vinylpyridine, polar polyamides, methyl cellulose, hydroxypropyl cellulose, hydroxyethyl cellulose, hydroxypropyl methylcellulose, ethylhydroxyethylcellulose, carboxymethyl cellulose, cellulose acetate, cellulose acetate butyrate, cellulose acetate propionate, cellulose nitrate, polyvinyl acetate, polyvinyl alcohol, copolymers of polyvinylacetate and polyvinyl alcohol, hydroxylmodified copolymers of vinyl acetate and vinylchloride, polyesters and polyurethanes containing at least 10% by weight of polyethylene oxide, styrene/methacrylic acid/hydroxyethyl methacrylate copolymers, styrene/methacrylic acid/hydroxypropyl methacrylate copolymers, methylmethacrylate/methacrylic acid copolymers, ethyl methacrylate/styrene/methacrylic acid copolymers, ethyl methacrylate/methyl methacrylate/styrene/methacrylic acid copolymers, polytetrafluoroethylene, hydrophilic cellulose copolymers, and mixtures thereof.

Indicator 120 provides a calorimetric reaction upon exposure to the gases produced by the growth of bacterial microorganisms. Gases, which are produced by the growth of microorganisms, include but are not limited to carbon dioxide, ammonium, hydrogen sulfide, sulfur dioxide, and hydrogen. Lactate may also be produced as a result of metabolic growth to subsequently form lactic acid. In a moist environment, as is the state beneath the wound dressing or catheter insertion site, these gases will form an acid (e.g., carbonic, sulfuric acid) or a base (e.g., ammonia) which reacts with the selected indicator to produce a calorimetric reaction that is easily visualized through barrier membrane 114, thereby alerting a user, such as an attending healthcare professional, of potentially harmful bacterial growth at the catheter insertion site.

The term "indicator" is used to describe chemical compounds which may be added to or coated onto polymeric compositions according to the present invention in amounts effective to detect gases which are produced as byproducts from the growth of microorganisms such as bacterial growth that may be beneath the wound dressing and within the puncture site of the skin from a central venous catheter insertion. Indictors are chemical compounds that undergo a chemical reaction in the presence of a gas or an acid or base conjugate of a gas and produce a calorimetric species in response to the acid or base produced. The chemical response of the indicator is generally concentration dependent. Indicators for use in the present invention may be solids or liquids. In the present invention, gases which are produced as normal byproducts of bacteria or microorganism growth (e.g., carbon dioxide, sulfur dioxide, lactate, and hydrogen) react with the chosen indicator which has been polymerized or dispersed throughout the polymeric composition. The indicator produces a calorimetric reaction upon exposure to the gas or an acid or base conjugate of the gas, thus indicating the presence of bacterial growth beneath the wound dressing or catheter insertion site and in close association with the indwelling central venous or other catheter.

Examples of indicators that may be used in the present invention include but are not limited to phenol red, xylenol blue, bromocresol purple, bromocresol green, Congo red, cresol red, phenolphthalien, bromothymol blue, p-naphtholbenzein, neutral red, a mixture of potassium iodide, mercuric (III) iodide, sodium borate, sodium hydroxide and water nile blue, thymolphthalein, crysol violet, hydroxy naphthol blue, malachite green oxalate, methyl orange, alizarin, crystal violet, methyl red, and mixtures thereof.

The compositions for use in the present invention include polymers, which are comprised of substantial quantities of monomers having polar groups associated with them, such that overall polymeric composition is rendered hydrophilic. Preferably, the polymeric compositions are comprised of monomers which contain for example, hydroxyl groups, ester groups, amide groups, urethane groups, or carboxylate groups. While not being limited by way of theory, it is believed that the inclusion of polar groups allows water to more readily permeate the polymer and consequently, bring dissolved gases into proximity of the indicator contained within the two membranes and evoke a reaction.

Membranes 114 and 118 may be chemically/physically functionalized (e.g., to include different functional exchange groups with different backbone) to allow for selective control over passage through the membrane (e.g., to allow specific molecules to pass and/or for molecules to pass in a specific direction (e.g., away from or toward the wound site)).

The two polymer membranes 114 and 118 "sandwich" indictor 120 for detecting the byproducts of bacterial growth such as gaseous carbon dioxide, lactic acid, ammonium, hydrogen sulfide, sulfur dioxide, and hydrogen in a dissolved aqueous or vapor state, thereby evoking a change in the color of the indicator if the pH of the immediate environment beneath the wound dressing or catheter insertion site changes, thereby signaling the presence/growth of harmful or potentially harmful bacterial microorganisms. Thus, in one example, a gas released by bacterial microorganisms selected from the group consisting of carbon dioxide, hydrogen sulfide, sulfur dioxide, ammonia, lactate, and mixtures thereof, may dissolve in water or water vapor that has permeated through the permeable membrane, to form one of carbonic acid, sulfuric acid, ammonium hydroxide, lactic acid, and mixtures thereof, thereby causing a pH change and interacting with the indicator to cause a calorimetric change.

Advantageously, the present invention provides an "early warning" of the growth of infectious microbial pathogens beneath the wound dressing at the site of catheter insertion. The indicator(s) employed in the invention reacts to a change in the pH resulting from the byproducts of microbial growth beneath the wound dressing or catheter insertion site and causes a distinct calorimetric change that can be easily visualized through transparent barrier membrane 114.

The present invention may be packaged in various ways and in one embodiment is packaged similarly to a dressing apparatus trademarked as Tegaderm®, available from 3M Health Care Ltd., of St. Paul, Minn. Optionally, barrier membrane 114, indicator 120, and permeable membrane 118 may be packaged between sheet liners 102 and 110 to facilitate application of the wound dressing and indicator to the surface of the skin over the site of the indwelling central venous or other catheter.

In one example, sheet liner 102 is a thin and rigid sheet of thin card on the barrier side or top side of barrier membrane 114, with "wings" 104 at each end. Sheet liner 102 may include a window 106 pre-cut such that window 106 may be peeled away to reveal barrier membrane 114 underneath, thus leaving barrier membrane 114, indicator 120, and permeable membrane 118 suspended on a frame of sheet liner 102, which facilitates precise placement of the film and reduces wrinkling. Accordingly, window 106 may be peeled away and removed just prior to application of apparatus 100 to the skin and allows for visualization of the catheter insertion site through the two transparent membranes 114 and 118 and indicator 120. Sheet liner 102 may also include a slit 108 along one side of the border of sheet liner 102 to allow for the peeling away of the border after the wound dressing is firmly applied to the skin at the site of the catheter insertion.

In a further example, sheet liner 110 is printed sheet of release paper coupled to the adhesive 116 adjacent to permeable membrane 118. Sheet liner 110 may also have wings 112 to aid in application to the skin. Sheet liner 110 is removed just after window 106 of sheet liner 102 is removed, and the wound dressing applied to the skin over the catheter site.

It will be apparent that the elements of detection apparatus 100 that contact the skin, including but not limited to the barrier membrane, the adhesive, and the permeable membrane, are composed of medical grade materials and in one example meet the requirements for long-term skin contact as established by the United States Food and Drug Administration.

By empirical data, growth of certain bacteria under controlled conditions may be correlated to pH such that the bacteria detection apparatus of the present invention may be calibrated for different sensitivities (e.g., to show a calorimetric change at an earlier time) or for different types of bacteria.

Embodiments described above illustrate but do not limit the invention. It should also be understood that numerous modifications and variations are possible in accordance with the principles of the present invention. For example, the elements of a bacterial growth detection apparatus, such as the membranes, indicator, and window, may have various sizes and shapes. Accordingly, the scope of the invention is defined only by the following claims.

I claim:

1. An apparatus for monitoring bacterial growth proximate to a catheter insertion site which apparatus comprises:
   1) a catheter and
   2) a catheter insertion site covering, wherein the catheter insertion site covering comprises:
      a barrier membrane;
      a permeable membrane for placement proximate to the catheter insertion site; and
      an indicator between the barrier membrane and the permeable membrane which is capable of indicating the presence of bacterial growth proximate to the permeable membrane.

2. The apparatus of claim 1, wherein the barrier membrane is a transparent hydrophobic polymeric membrane.

3. The apparatus of claim 1, wherein the barrier membrane is comprised of material selected from the group consisting of poly(vinylidene fluoride), poly(vinylidene chloride), phenoxy resins, butadiene/styrene copolymers, butadiene/methylstyrene copolymers, poly(meth)acrylates, butadiene/acrylonitrile copolymers, ethylene/propylene copolymers, polybutadiene, polyisoprene, poly(oxy-2,6-dimethyl-1,4-phenylene), poly(oxycarbonyloxy-1,4[1,4-phenyleneisopropylidene-1,4-phenylene), acrylonitrile styrene copolymers, acrylonitrile/methyl acrylate/butadiene copolymers, acrylonitrile/styrene/butadiene copolymers, poly-1-vinylaphthalene, polyvinylphenyl ketone, poly-p-xylylenedodecanedioate, poly-tetramethylene octenediamide, poly-tetramethylene terephthalene, poly-trimethylene-3,3'-dibenzoate, poly-terephthallic anhydride, poly-4-methyldiamine, polyvinylene carbonate, polyvinylene laurate, polyisopropenyl acetate, polyallylbenzene, polyvinylbutyl ether, polyvinyl formate, polyvinyl phenyl ether, polynorbornadine, polycarbonate, hydrophobic polyesters and polyurethanes, and mixtures thereof.

4. The apparatus of claim 1, wherein the permeable membrane is a transparent hydrophilic polymeric membrane.

5. The apparatus of claim 1, wherein the permeable membrane is permeable or semi-permeable.

6. The apparatus of claim 1, wherein the permeable membrane is comprised of material selected from the group consisting of (poly)hydroxyethyl methacrylate, (poly)hydroxypropyl methacrylate, (poly)glycerol methacrylate, copolymers of hydroxyethyl methacrylate, hydroxypropyl methacrylate or glycerol methacrylate and methacrylic acid, aminoacrylate and aminomethacrylate, (poly)vinylpyridine, polar polyamides, methyl cellulose, hydroxypropyl cellulose, hydroxyethyl cellulose, hydroxypropyl methylcellulose, ethylhydroxyethylcellulose, carboxymethyl cellulose, cellulose acetate, cellulose acetate butyrate, cellulose acetate propionate, cellulose nitrate, polyvinyl acetate, polyvinyl alcohol, copolymers of polyvinylacetate and polyvinyl alcohol, hydroxyl modified copolymers of vinyl acetate and vinylchloride, polyesters containing at least 10% by weight of polyethylene oxide, polyurethanes containing at least 10% by weight of polyethylene oxide, styrene/methacrylic acid/hydroxyethyl methacrylate copolymers, styrene/methacrylic acid/hydroxypropyl methacrylate copolymers, methylmethacrylate/methacrylic acid copolymers, ethyl methacrylate/styrene/methacrylic acid copolymers, ethyl methacrylate/methyl methacrylate/styrene/methacrylic acid copolymers, polytetrafluoroethylene, hydrophilic cellulose copolymers, and mixtures thereof.

7. The apparatus of claim 1, wherein the indicator detects pH change associated with byproducts of bacterial growth selected from the group consisting of gaseous carbon dioxide, hydrogen sulfide, sulfur dioxide, hydrogen, ammonium, lactate, and mixtures thereof.

8. The apparatus of claim 1, wherein the indicator detects pH change from the formation of carbonic acid, sulfuric acid, ammonium hydroxide, lactic acid, or mixtures thereof.

9. The apparatus of claim 1, wherein the indicator is comprised of material selected from the group consisting of phenol red, xylenol blue, bromocresol purple, bromocresol green, Congo red, cresol red, phenolphthalien, bromothymol blue, p-naphtholbenzein, neutral red, a mixture of potassium iodide, mercuric (III) iodide, sodium borate, sodium hydroxide and water nile blue, thymolphthalein, crysol violet, hydroxy naphthol blue, malachite green oxalate, methyl orange, alizarin, crystal violet, methyl red, and mixtures thereof.

10. The apparatus of claim 1, wherein the indicator is capable of indicating the presence of bacterial growth byproducts proximate the permeable membrane by a color change in the indicator.

11. The apparatus of claim 1, wherein the associated bacteria is selected from the group consisting of *Staphylococcus aureus, Staphylococcus epidermitus, Streptococcus mitis, Streptococcus sanguis, Enterococcus faecium, Escherichia coli, Enterobacter cloacae, Enterobacter aerogenes, Enterococcus faecalis, Pseudomonas aeruginosa, Klebsiella pneumonia, Candida albicans*, gram negative bacilli, and combinations thereof.

12. The apparatus of claim 1, further comprising a first sheet liner adjacent the barrier membrane and a second sheet liner adjacent the permeable membrane.

13. The apparatus of claim 1, further comprising an adhesive coupling the barrier membrane, the indicator, and the permeable membrane.

14. An apparatus for monitoring bacterial growth proximate to a catheter insertion site which apparatus comprises:
1) a catheter and
2) a catheter insertion site covering, wherein the catheter insertion site covering comprises:
a barrier membrane including a transparent hydrophobic polymeric membrane;
a permeable membrane including a transparent hydrophilic polymeric membrane, the permeable membrane for placement proximate to the catheter insertion site; and
an indicator between the barrier membrane and the permeable membrane, the indicator capable of detecting a pH change caused by byproducts of bacterial growth which come in contact with said indicator.

15. The apparatus of claim 14, wherein the barrier membrane is comprised of material selected from the group consisting of poly(vinylidene fluoride), poly(vinylidene chloride), phenoxy resins, butadiene/styrene copolymers, butadiene/methylstyrene copolymers, poly(meth)acrylates, butadiene/acrylonitrile copolymers, ethylene/propylene copolymers, polybutadiene, polyisoprene, poly(oxy-2,6-dimethyl-1,4-phenylene), poly(oxycarbonyloxy-1,4[1,4-phenyleneisopropylidene-1,4-phenylene), acrylonitrile styrene copolymers, acrylonitrile/methyl acrylate/butadiene copolymers, acrylonitrile/styrene/butadiene copolymers, poly-1-vinylaphthalene, polyvinylphenyl ketone, poly-p-xylylenedodecanedioate, poly-tetramethylene octenediamide, poly-tetramethylene terephthalene, poly-trimethylene-3,3'-dibenzoate, poly-terephthallic anhydride, poly-4-methyl-diamine, polyvinylene carbonate, polyvinylene laurate, polyisopropenyl acetate, polyallylbenzene, polyvinylbutyl ether, polyvinyl formate, polyvinyl phenyl ether, polynorbornadine, polycarbonate, hydrophobic polyesters and polyurethanes, and mixtures thereof.

16. The apparatus of claim 14, wherein the permeable membrane is permeable or semi-permeable.

17. The apparatus of claim 14, wherein the permeable membrane is comprised of material selected from the group consisting of (poly)hydroxyethyl methacrylate, (poly)hydroxypropyl methacrylate, (poly)glycerol methacrylate, copolymers of hydroxyethyl methacrylate, hydroxypropyl methacrylate or glycerol methacrylate and methacrylic acid, aminoacrylate and aminomethacrylate, (poly)vinylpyridine, polar polyamides, methyl cellulose, hydroxypropyl cellulose, hydroxyethyl cellulose, hydroxypropyl methylcellulose, ethylhydroxyethylcellulose, carboxymethyl cellulose, cellulose acetate, cellulose acetate butyrate, cellulose acetate propionate, cellulose nitrate, polyvinyl acetate, polyvinyl alcohol, copolymers of polyvinylacetate and polyvinyl alcohol, hydroxyl modified copolymers of vinyl acetate and vinylchloride, polyesters containing at least 10% by weight of polyethylene oxide, polyurethanes containing at least 10% by weight of polyethylene oxide, styrene/methacrylic acid/hydroxyethyl methacrylate copolymers, styrene/methacrylic acid/hydroxypropyl methacrylate copolymers, methyl-methacrylate/methacrylic acid copolymers, ethyl methacrylate/styrene/methacrylic acid copolymers, ethyl methacrylate/methyl methacrylate/styrene/methacrylic acid copolymers, polytetrafluoroethylene, hydrophilic cellulose copolymers, and mixtures thereof.

18. The apparatus of claim 14, wherein the byproducts of bacterial growth is selected from the group consisting of gaseous carbon dioxide, hydrogen sulfide, sulfur dioxide, hydrogen, ammonium, lactate, and mixtures thereof.

19. The apparatus of claim 14, wherein the indicator detects pH change from the formation of carbonic acid, sulfuric acid, ammonium hydroxide, or lactic acid.

20. The apparatus of claim 14, wherein the indicator is comprised of material selected from the group consisting of phenol red, xylenol blue, bromocresol purple, bromocresol green, Congo red, cresol red, phenolphthalien, bromothymol blue, p-naphtholbenzein, neutral red, a mixture of potassium iodide, mercuric (III) iodide, sodium borate, sodium hydroxide and water nile blue, thymolphthalein, crysol violet, hydroxy naphthol blue, malachite green oxalate, methyl orange, alizarin, crystal violet, methyl red, and mixtures thereof.

21. The apparatus of claim 14, wherein the indicator is capable of indicating the presence of bacterial growth byproducts proximate the permeable membrane by a color change in the indicator.

22. The apparatus of claim 14, wherein the bacteria is selected from the group consisting of *Staphylococcus aureus, Staphylococcus epidermitus, Streptococcus mitis, Streptococcus sanguis, Enterococcus faecium, Escherichia coli, Enterobacter cloacae, Enterobacter aerogenes, Enterococcus faecalis, Pseudomonas aeruginosa, Klebsiella pneumonia, Candida albicans*, gram negative bacilli, and combinations thereof.

23. The apparatus of claim 14, further comprising a first sheet liner adjacent the barrier membrane and a second sheet liner adjacent the permeable membrane.

24. The apparatus of claim 14, further comprising an adhesive coupling the barrier membrane, the indicator, and the permeable membrane.

* * * * *